(12) United States Patent
Oddsen et al.

(10) Patent No.: US 6,254,624 B1
(45) Date of Patent: Jul. 3, 2001

(54) EXTERNAL TISSUE EXPANSION DEVICE FOR BREAST RECONSTRUCTION, MALE PATTERN BALDNESS AND REMOVAL OF NEVI AND KELOIDS

(75) Inventors: Robert Oddsen, Centerport; Ralph Ger, Lake Success, both of NY (US)

(73) Assignee: Progressive Surgical Products, Westbury, NY (US)

( * ) Notice: Subject to any disclaimer, the term of this patent is extended or adjusted under 35 U.S.C. 154(b) by 0 days.

(21) Appl. No.: 09/413,586

(22) Filed: Oct. 6, 1999

Related U.S. Application Data

(60) Provisional application No. 60/103,277, filed on Oct. 6, 1998.

(51) Int. Cl.[7] .................................................. A61B 17/04
(52) U.S. Cl. .................... 606/213; 606/150; 606/212; 606/215; 606/216; 606/217
(58) Field of Search ................................... 606/148, 150, 606/151, 212, 213, 215–218

(56) References Cited

U.S. PATENT DOCUMENTS

| | | | |
|---|---|---|---|
| 4,535,772 | 8/1985 | Sheehan | 128/337 |
| 4,828,560 | 5/1989 | Heyler, III | 623/8 |
| 4,950,292 | 8/1990 | Audretsch | 623/8 |
| 5,109,875 | 5/1992 | Gottlieb | 128/899 |
| 5,127,412 | 7/1992 | Cosmetto et al. | 128/898 |
| 5,163,948 | 11/1992 | Kummer | 606/152 |
| 5,441,540 | 8/1995 | Kim | 623/66 |
| 5,486,196 | 1/1996 | Hirshowitz et al. | 606/218 |
| 5,507,775 | 4/1996 | Ger et al. | 606/216 |
| 5,531,790 | 7/1996 | Frechet et al. | 623/15 |
| 5,549,713 | 8/1996 | Kim | 623/66 |
| 5,556,428 | 9/1996 | Shah | 623/13 |
| 5,562,705 | 10/1996 | Whiteford | 606/215 |
| 5,618,310 | 4/1997 | Ger et al. | 606/216 |

FOREIGN PATENT DOCUMENTS

| | | |
|---|---|---|
| 2001597 | 10/1993 | (RU) . |
| 1669440 | 8/1991 | (SU) . |

*Primary Examiner*—Gary Jackson
(74) *Attorney, Agent, or Firm*—Steinberg & Raskin, PC

(57) ABSTRACT

An external tissue expansion device applies constant continuous low grade force to skin to obtain additional tension free skin and subcutaneous tissue prior to a surgical procedure. The device consists of two suture plates each being laminated structure of steel and an adhesive attached foam cushion. On the each end of one suture plate is a housing that contains a constant force spring placed over a post. The ends of the constant force spring protrude from the housing and there is a hook attached to the end of the constant force spring. On each end of the other suture plate there is a housing, with a opening that can accept the hook of the opposite suture plate. These suture plates are constructed so that they can be manually shaped to conform to the topography of the body part to be corrected and are attached to skin near the defect to be corrected prior to a surgical procedure. When the hooks from one suture plate are inserted into the openings of the housing of the other suture plate, the constant force springs pulls the suture plates together and over a time period stretches and expands skin and subcutaneous tissue external from the suture plates and accumulates this additional tension free skin and subcutaneous tissue in the opening between the two suture plates. This invention further provides a method to permit breast reconstruction without the use of any prosthesis, whereby a surgeon expands a breast mound of the patient's own body tissue at a specific location consisting of tension free skin and subcutaneous tissue and shapes this breast mound into a breast.

20 Claims, 12 Drawing Sheets

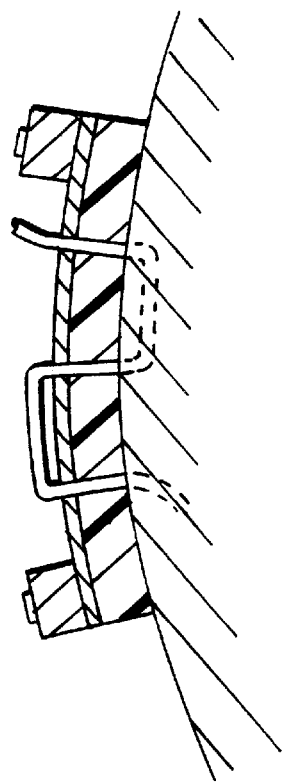
FIG. 1B1
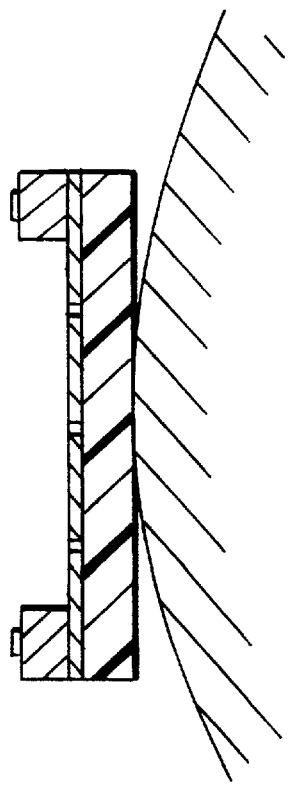
FIG. 1B2

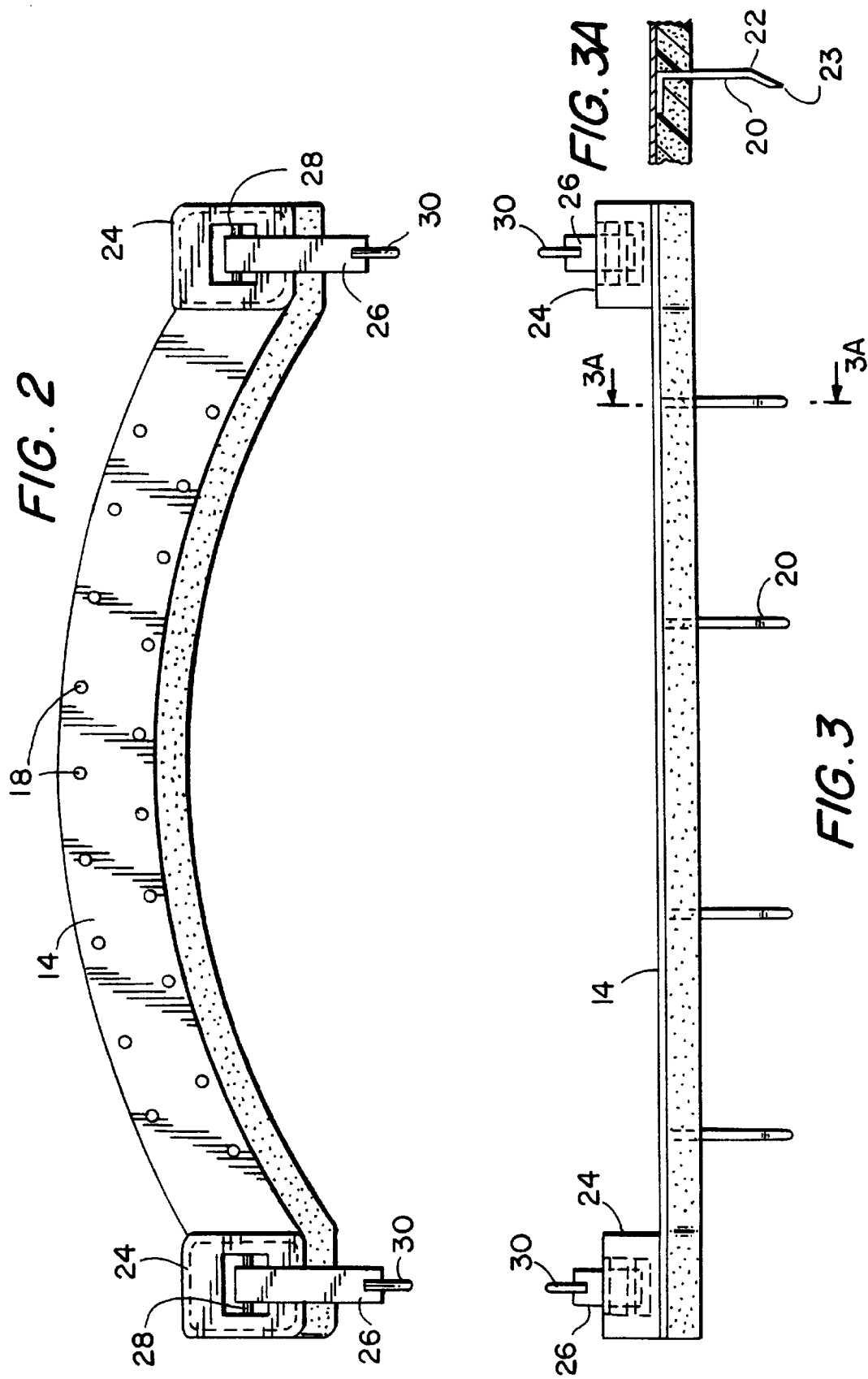

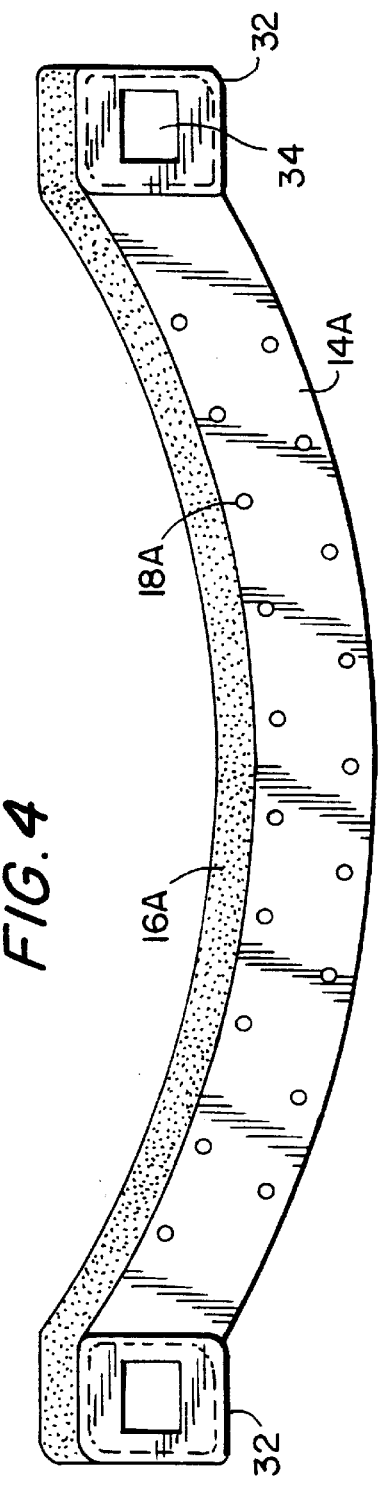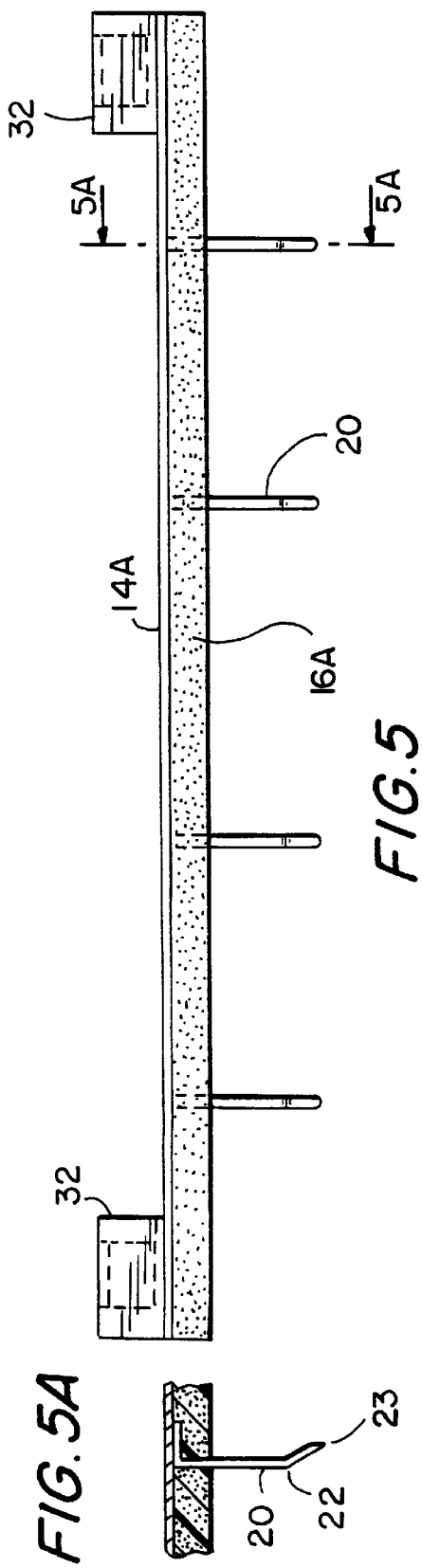

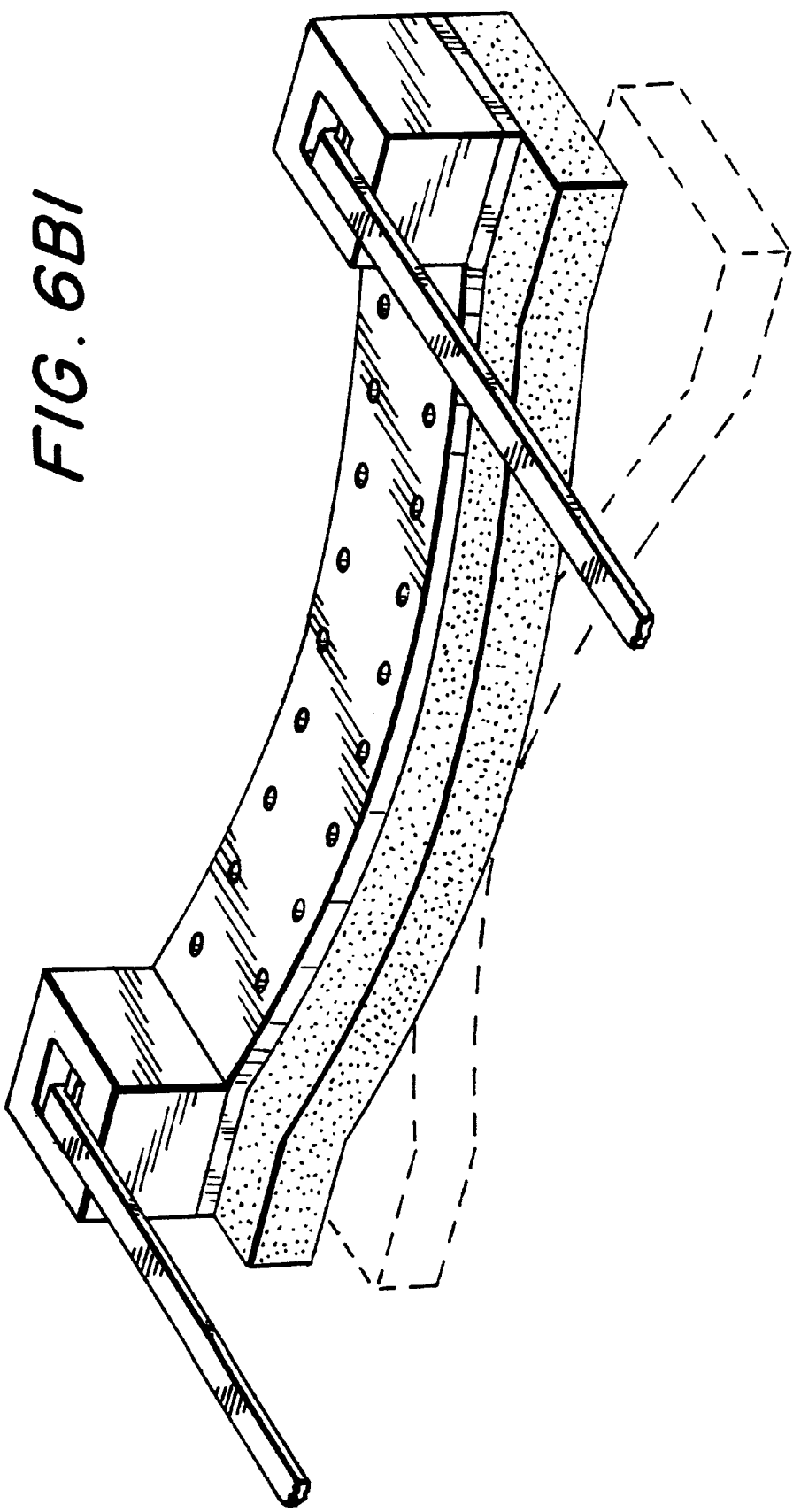

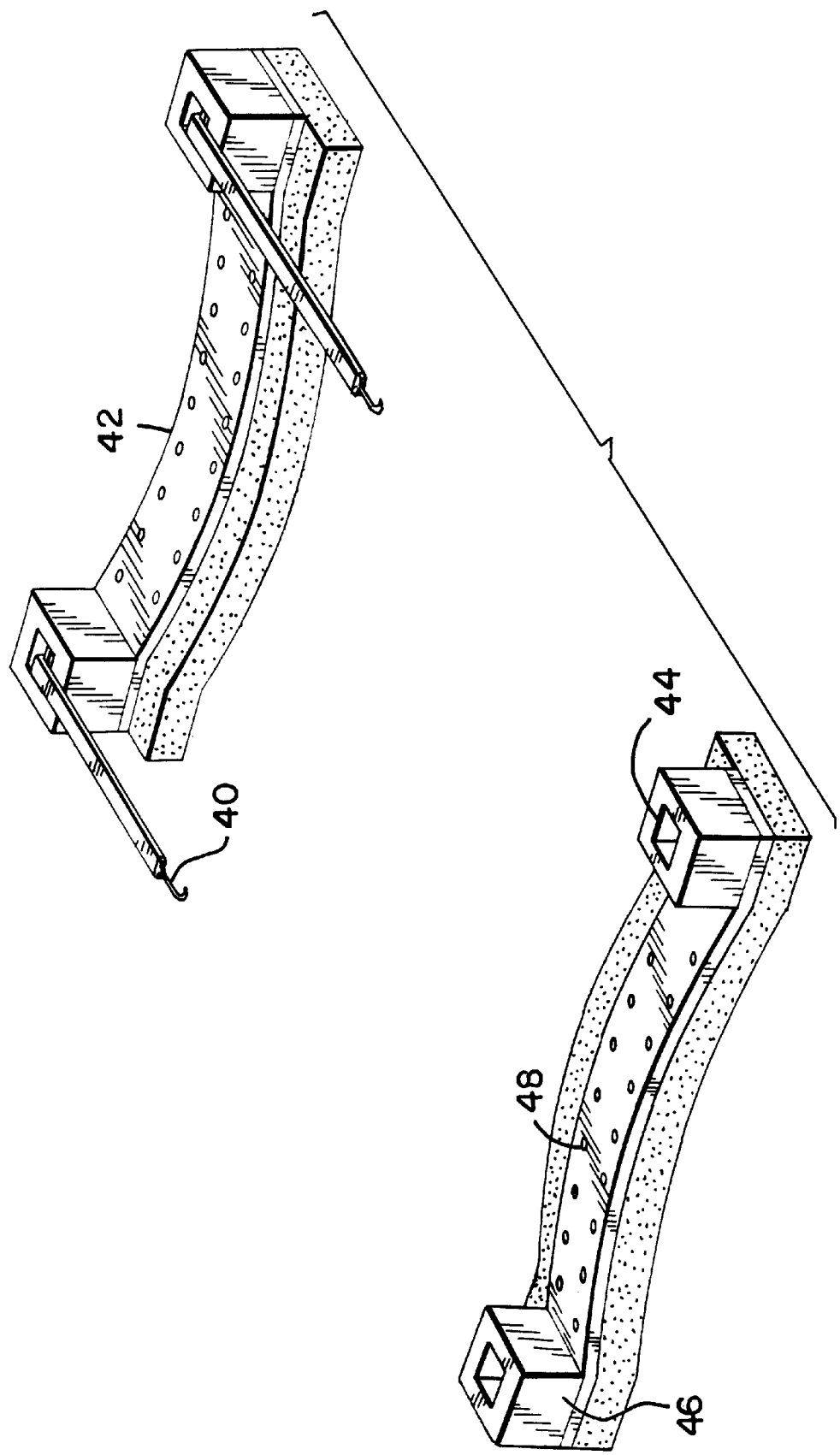

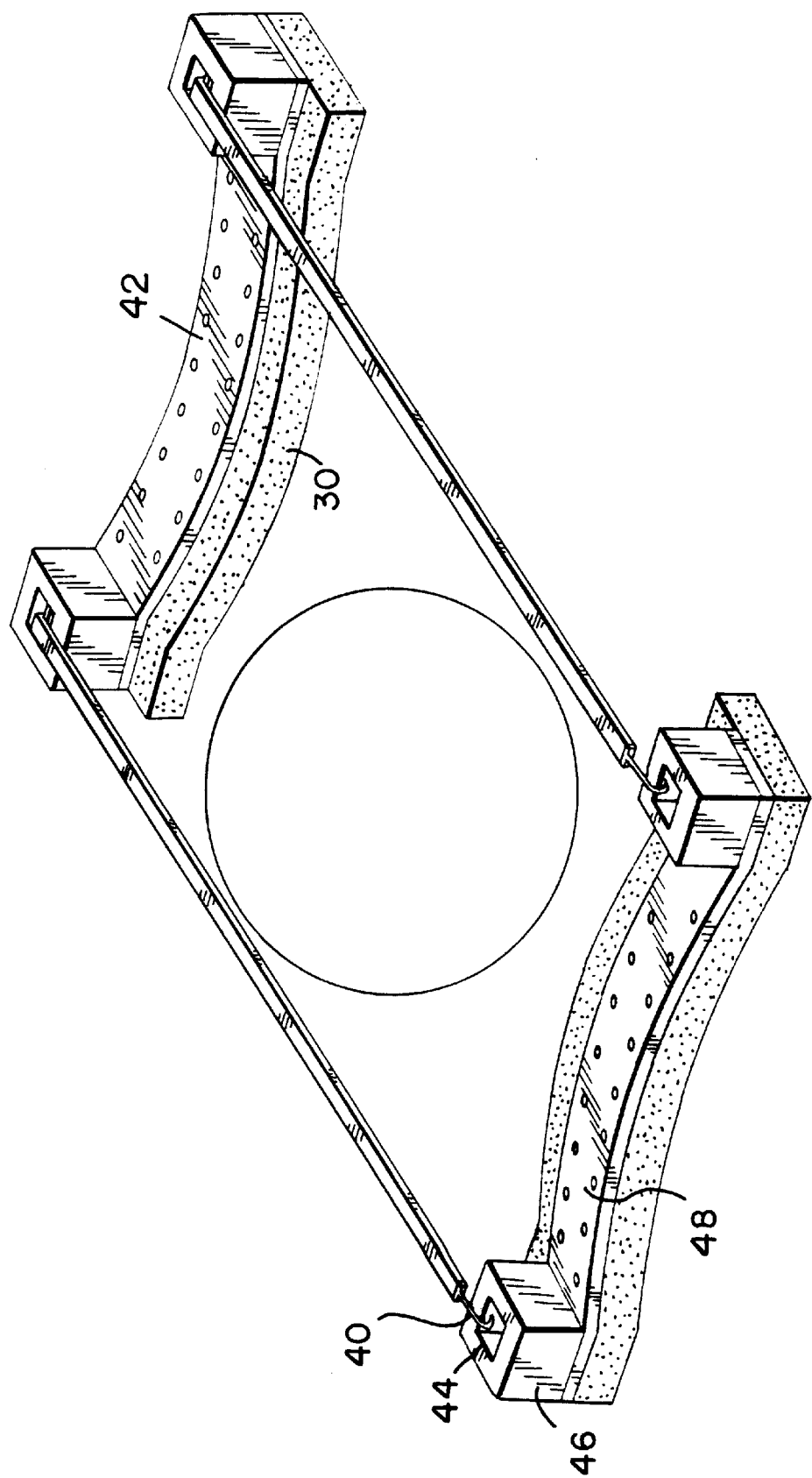

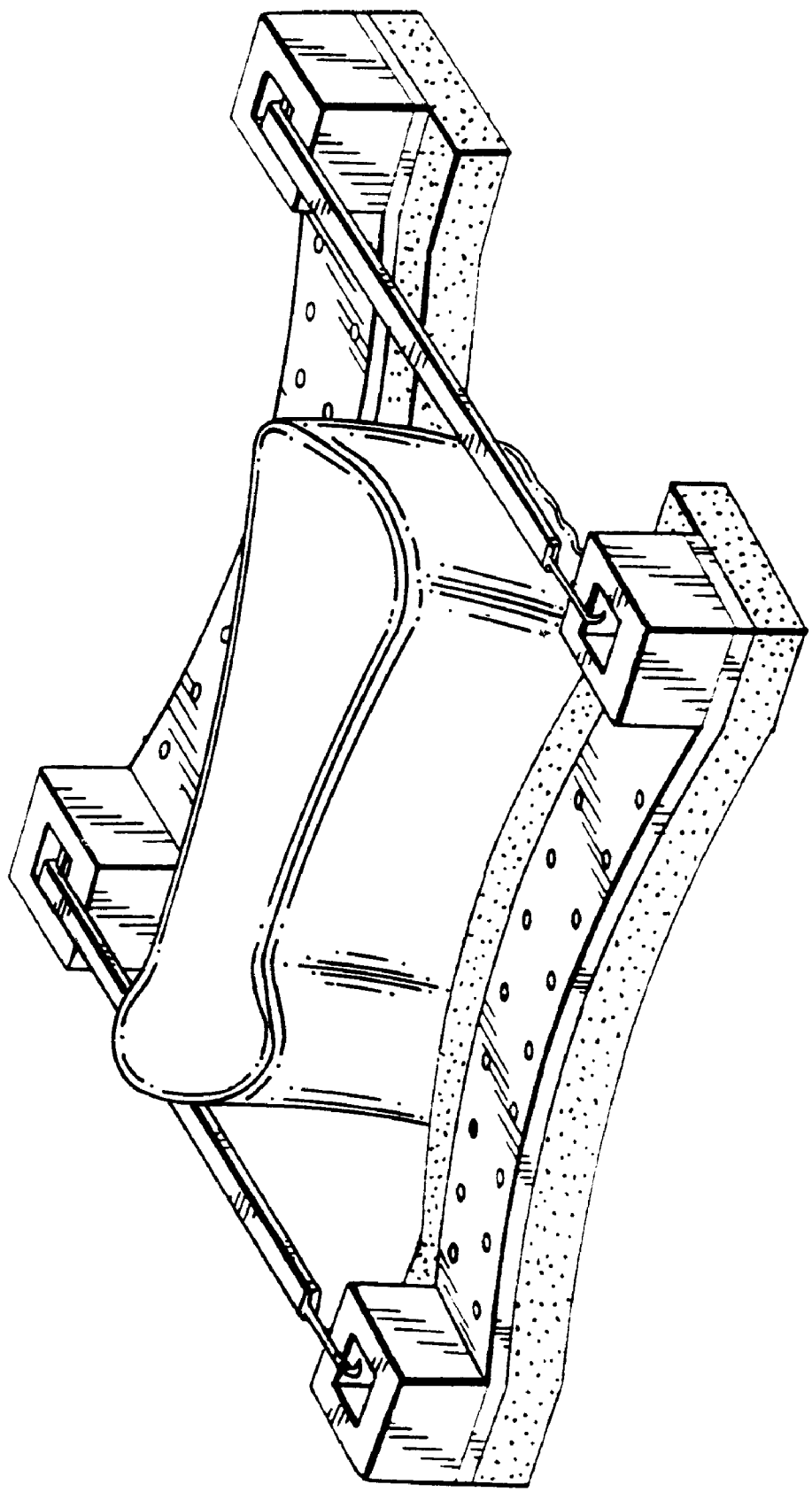

EXTERNAL TISSUE EXPANSION DEVICE FOR BREAST RECONSTRUCTION, MALE PATTERN BALDNESS AND REMOVAL OF NEVI AND KELOIDS

This application claims benefit of Provisional Application 60/103,277 filed Oct. 6, 1998.

FIELD OF THE INVENTION

This invention is in the field of medical devices and techniques of tissue expansion that are used by plastic and general surgeons to obtain additional tension free skin and subcutaneous tissue prior to a surgical procedure to correct a defect or to cover an implantable prosthesis. Such surgical procedures include breast augmentation and breast reconstruction after mastectomy, removal of a nevus or keloid, removal of malignant or benign lesions, improvement of cosmetic appearance and other plastic reconstructive procedures of the body that require tension free skin and subcutaneous tissue without distortion of nearby body structures. Also the new invention can be used in new surgical procedures to correct male pattern baldness and for breast reconstructive surgery and removal of nevus, hypertrophic scars or keloids..

BACKGROUND

It is a surgical axiom that wound tension should be avoided at all costs. In surgical procedures a certain amount of skin may be excised and easily closed but there is a point beyond which closure results in wound tension or the wound cannot be closed resulting in a deficit of skin. Skin tension is of particular importance in wound healing because a highly stressed wound environment delays wound healing. A wound sutured closed under tension will result in maximum scarring. Wound tension is also one of the factors for initiation of a keloid or hypertropic scar. For the plastic surgeon the qualitative end result is one of the most crucial factors in reconstructive surgery. The attention to minute details can be the difference between success and failure for plastic surgical procedures where cosmetic appearance is a critical factor. Tension free skin is especially important in facial areas or when skin coverage is required to cover a prosthesis. Wounds closed under tension can create distortions of nearby facial features such as eyelids, lips, etc., create wide displeasing scars or result in exposure of an implantable prosthesis.

The physician has three surgical means to obtain additional tension free skin namely: (A) skin grafts, (B) free flaps and (C) internally placed tissue expansion devices.

A. Skin grafts involve the transfer from a donor site, the epidermis and a measured portion of the dermis to a recipient site formed as a shallow well-vascularized wound. The donor site will take as long as three weeks to heal. Skin grafts provide superficial coverage and do not replace deeper tissue layers such as subcutaneous tissue. With skin grafts there is no satisfactory match in color, texture or thickness to harmonize with surrounding tissue.

B. Tissue flaps are used in the procedures that involve the transfer of skin and underlying structures such as subcutaneous tissue, fascia and muscle to fill a defect. This procedure involves detachment of the tissue from its original site, transfer of the flap to the defect, and suture of the flap over the defect. In a free flap the flap tissue is completely removed from the donor site and reattached to the wound using microvascular techniques. In all other flap procedures there is a base which remains attached and supplies circulatory support for the flap.

C. Present internal tissue expansion devices have at least three disadvantages: (1) they involve multi-staged surgical operations, (2) they sacrifice the well being of the donor site for the need of the recipient site, (3) and the time between first and second surgical procedure can be as long as one to four months. Present internal tissue expanders are essentially inflatable balloons or pouches that are surgically placed into and under subcutaneous tissue in an area close to the defect to be corrected. After a time period for the surgical incision to heal, pressure and volume of the pouch/balloon is incrementally increased by injections of saline into the pouch/balloon. With this technique excessive stresses are placed on the skin due to the high forces exerted by the internal tissue expander. The typical method of determining expansion pressure is measured by pain response from the patient. While these stresses are initially high, the force levels dissipate as the skin stretches necessitating cyclic injections of saline into the pouch/balloon over weekly time periods to create additional new skin. When a sufficient amount of skin is created the pouch/balloon is removed, and the new skin is incised and the donor site closed by suture. This new skin is sutured to cover the defect which results in a tension free closure of the wound. Tissue expansion with internally placed tissue expanders has a 38% complication rate. Incisional dehiscence and exposure of the internal expander is a major complication of internally placed tissue expanders. Other complications such as leakage of fluid, necrosis of skin, hematoma and spontaneous deflation of the expander may cause abandonment of the procedure. The frequency of saline precutaneous injections of sterile saline predispose the implant cavity to infection which is serious and involves removal of the internal expander. The internally placed expander is a foreign body, and particles from the expander which delaminate or flake from the surface into the implant cavity and tissue cause an inflammatory reaction.

RELEVANT PRIOR ART

U.S. Pat. No. 5,618,310; Inventors: Ralph Ger & Robert Oddsen.

U.S. Pat. No. 5,507,775; Inventors: Ralph Ger & Robert Oddsen.

SUMMARY OF THE NEW INVENTION

The ideal tissue expansion device would not require a subcutaneous implant cavity for the expander, would eliminate the complications of surgical procedures, would quickly obtain additional tension free skin and subcutaneous tissue, and would obtain skin that is a satisfactory match in color, thickness and texture to harmonize with the surrounding tissue. The Ger-Oddsen device is an external tissue expansion device that achieves all these objectives. It is attached by means of sutures, staples or tissue hooks to the area where tension free skin and subcutaneous tissue is required, there is no incisional surgery and the device quickly obtains additional tension free skin and subcutaneous tissue in days versus weeks when compared to internally placed tissue expanders. The Ger-Oddsen device applies an external force that is constant, continuous and low grade. Constant force to skin has been demonstrated to expand more tissue than the intermittent applications of force. Also constant continuous force achieves the most rapid rate of accumulation of tissue.

BRIEF DESCRIPTION OF THE DRAWINGS

FIG. 1*b*1 shows an expansion plate of FIG. 1*b* in side elevation view before being bent to conform to the topography of the patient.

FIG. 1*b*2 is similar to FIG. 6*b*1 showing the expansion plate after being bent to conform to the topography and after being sutured to the patient.

FIG. 2 is a top front perspective view of one of the set of expansion plates which carries the Negator spring.

FIG. 3 is a front elevation view of FIG. 2.

FIG. 4 is a top, front perspective view of one of the set of expansion plates which receives the hook of the spring.

FIG. 5 is a front elevation view of FIG. 4.

FIG. 6*b*1 shows the expansion plate of FIG. 6*b* in its flat condition in solid line and in its bent condition in dotted line.

FIG. 7 is a schematic top perspective view of a set of unassembled expansion plates of the external tissue expansion device.

FIG. 8 is a schematic top perspective view of the set of tissue expansion plates of FIG. 7 assembled together about a region of baldness at the beginning of a procedure.

FIG. 10 is similar to FIG. 9 showing the assembled set of tissue expansion plates after an additional time period of application.

DETAILED DESCRIPTION OF THE PREFERRED EMBODIMENTS

The Ger-Oddsen device is an external tissue expander that utilizes a set of two expansion plates of a geometric shape to conform to the body part requiring additional tension free skin and subcutaneous tissue. Sheet 1 of the drawings shows schematically a female patient's closed mastectomy incision (FIG. 1*a*), a set of the new tissue expansion plates situated above and below the closed incision (FIG. 1*b*), progress of tissue expansion (FIG. 1*c*), and fully expanded tissue with the breast prosthesis implanted (FIG. 1*d*).

Figure 1B:
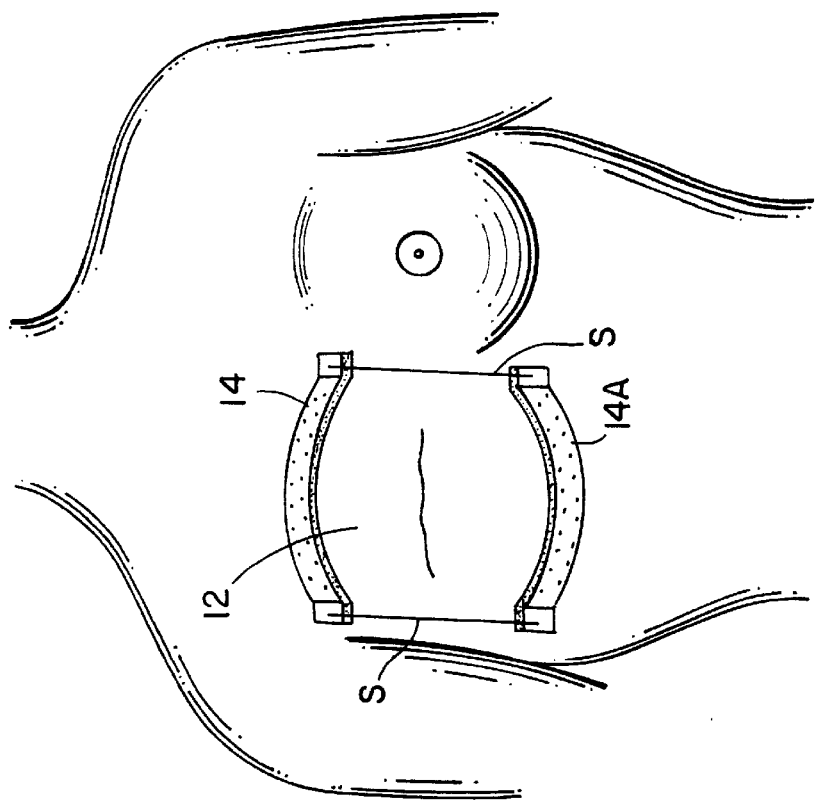
FIG. 1*b* is similar to FIG. 1*a* showing a tissue expansion device comprising a set of expander plates positioned above and below the mastectomy incision, one of said set carrying a pair of Negator springs and the other adapted to receive and hold the hook of each spring.
Figure 1A:
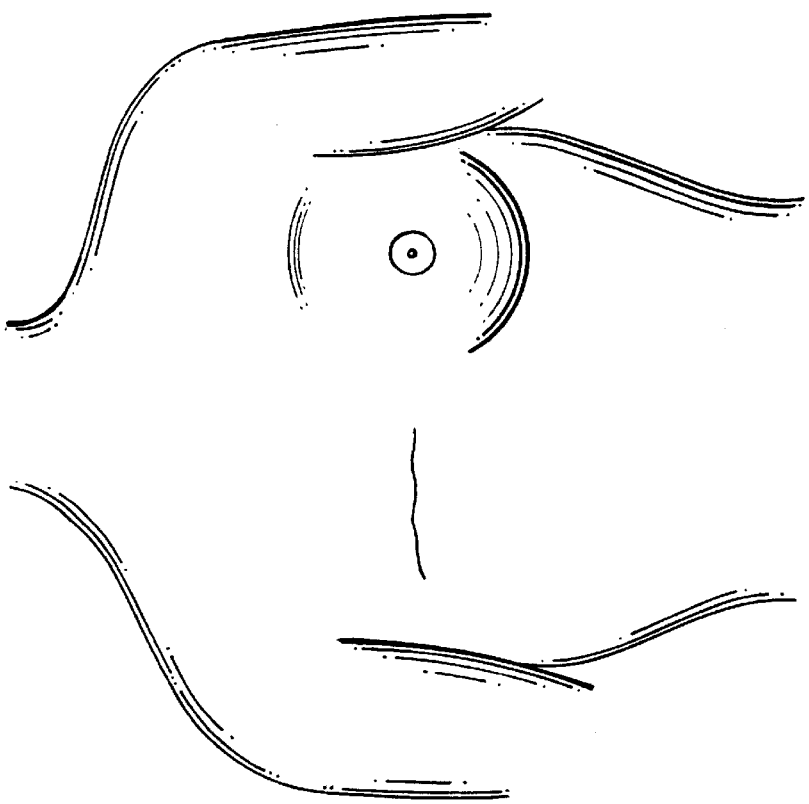
FIG. 1a is a partial front elevation view of a female patient showing a breast after closing of a mastectomy incision.
Figure 1D:
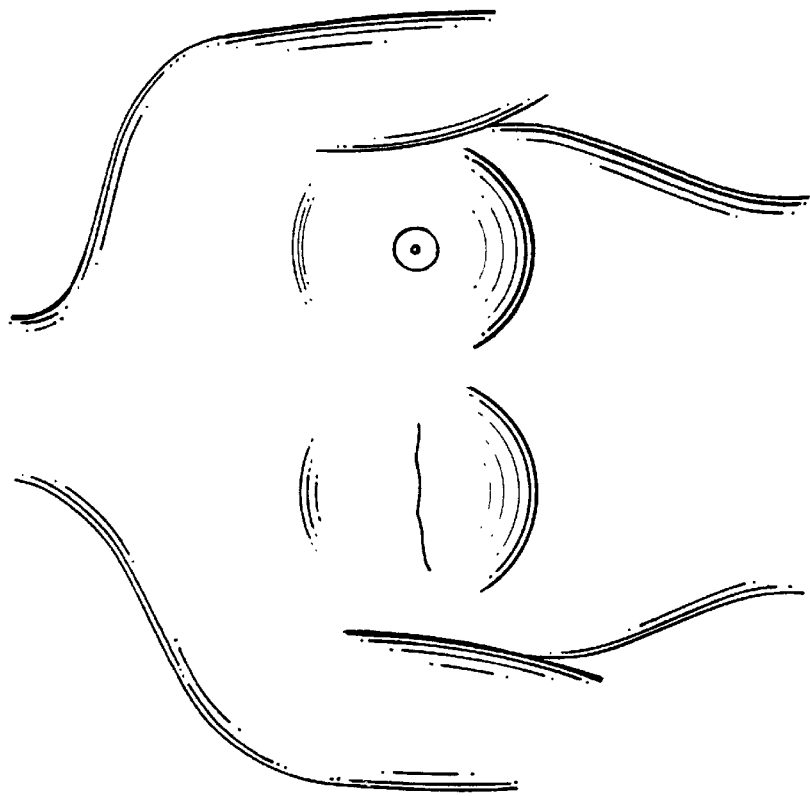
FIG. 1*d* is similar to FIG. 1*c* showing the breast area after removal of the tissue expansion device and implantation of a breast prothesis.

As seen in FIG. 1*b* the geometric curved shape of the tissue expansion plate for breast reconstruction is concave, approximately conforms to the circumference of the implantable definitive breast prosthesis, contralateral breast or breast shape desired by the patient and permits an area 12 for tension free skin and subcutaneous tissue to accumulate. Variations of this shape expansion plate (also called expander plate or suture plate) are used for the tissue expansion device for male pattern baldness as seen in FIG. 8 and described later herein.

In the Ger-Oddsen external tissue expander the set of two suture plates is seen in FIGS. 1*b*, 1*c* and 2–4. Each of the suture plates 14, 14A is a laminated structure consisting of a thin stainless steel plate 14 about 0.015 to 0.025 inch thick to which is attached a foam cushion which is about one quarter inch thick and made of cross-linked polyolefin foam or other appropriate cushion, preferably having an adhesive strip on the top side for attachment to the bottom surface of the expansion plate. The typical expansion plate has an arrangement of suture holes 18, 18A and/or tissue hooks 20 to permit the surgeon to fasten the suture plate to the skin. The function of the foam cushion component of the suture plate is to provide a soft surface for contact with the skin and to prevent necrosis of skin during the external tissue expansion process. The foam cushion is extends past the width of stainless steel plate 14 on the edge facing the mating expansion plate. When the physician fastens the suture plate to skin, the foam cushion is compressed and the foam cushion covers sharp edges of the stainless steel plate thereby preventing damage to skin during the stretching process. The stainless steel component of the suture plate provides the strength of the laminated suture plate. It is of a thickness, ductility and hardness that permits the surgeon to easily bend the plate to conform to the topography of the patient where the suture plates are secured to the patient and to retain this preset shape. It is of a width that allows minimum deflection during the pre-stretching tissue expansion procedure.

Attached to the suture plates are a number of tissue hooks 20 for use where there is a requirement for a significant amount of subcutaneous adipose tissue (breast reconstruction). The tissue hooks 20 are stainless steel wire about 0.036 inches in diameter, long and angled at the end 22 to grasp tissue and have sharpened points 24 for easy penetration into tissue. On each end of each stainless steel plate there is attached a housing 24 that contains a constant force spring 26 such as the Negator® type springs. The constant force spring 26 is placed over an internal post 28 inside the housing 24 and protrudes from the housing. The clearances between the steel post, the opening in the housing for the protruding constant force spring and the constant force spring are of a magnitude to insure at least a 20 degree lateral movement of the constant force spring to accommodate misalignment of suture plates when they are attached to the patient. On each end of the constant force spring is attached a hook 30. On each end of the other or receiving suture plate 14A there is attached a plastic housing 32 with an opening 34 into which the hook 30 of the constant force spring from the other suture plate 14 can be inserted.

The Ger-Oddsen external tissue expander allows the physician to pre-stretch skin and subcutaneous tissue prior to the removal of a defect or prior to insertion of an implantable prosthesis. It also allows the surgeon to create a mound of tension free skin and subcutaneous tissue at a specific location. The Ger-Oddsen external tissue expander is simple to use. The surgeon positions the suture plates near the defect to be corrected, bends the suture plates to conform to the topography of the area and fastens the two plates to the skin leaving an opening between the two suture plates for the tension free skin and subcutaneous tissue to accumulate. The surgeon then pulls the hooks at the end of the spring from one suture plate and inserts them into the holes of the housing on the other suture plate. When the hooks from one suture plate are inserted into the holes of the housing of the other suture plate, the constant force springs applies a continuous, sustained low grade force of constant magnitude which pulls the suture plates together. The suture plates automatically approach each other over a time period, and as the suture plates approach each other they direct the additional tension free skin and subcutaneous tissue into the space between the suture plates. After a time period of a few days the surgeon evaluates the patient to determine when enough additional tension free skin and subcutaneous tissue is obtained to correct the defect.

As discussed below these surgical procedures utilizing the external tissue expansion device is applicable for both breast reconstruction and treatment of male pattern baldness and the removal of nevi, hypertropic scars and keloids.

Breast Reconstruction

There are two types of surgical procedures available for breast reconstruction after mastectomy. One of these surgical procedures consists of an internal tissue expander or an expandable prosthesis that is placed in a complete submuscular pocket made by suturing the pectoralis major, with the serratus anterior and/or latissimus dorsi. This placement of the internal tissue expander is after the mastectomy and prior to closing the mastectomy incision. After a time period for the surgical incision to heal, pressure and volume of the internal tissue expander is incrementally increased by injections of saline into the internal tissue expander over weekly time periods to create additional new skin. When enough skin has been created the internal tissue expander is replaced with a definitive prosthesis. The time between the insertion of the expander and a permanent implant can vary from many weeks to some months.

Operative time of breast reconstruction using prostheses is about 1 hour. This procedure gives the best results in small and medium sized slight pthotic breast and an implant prosthesis of about 300 cc. Reconstruction with implants is often chosen by patients because of the decreased hospitalization, operating time and skin incisions. Tissue expanders cannot be used in cases of thin tight skin or in patients where a larger breast (over 300 cc) is required. In cases where additional skin is required after radical mastectomy or cases where there is thin tight skin, a surgical flap procedure is recommended.

The other type of surgical procedure available for breast reconstruction is the use of the patient's own body tissue by means of a flap procedure to create a breast mound. The most common type of surgical procedure is the TRAM (transverse rectus abdominis myocutaneous) flap which obtains a sufficient amount of tissue to permit breast reconstruction without the use of any prosthesis. The operative time using TRAM flap varies from 2 to 4 hours (mean 3.1 hours) with a postoperative stay of 11.2 days (range 6–18 days) and a 4–6 week convalescence. The selection of a patient suitable for a flap procedure depends on many factors including the condition of the skin and muscles of the chest wall, breast size and availability of donor flap sites. Middle aged women with contralateral large and/or photic breast and redundant lower abdomen are the best candidates for the TRAM flap.

The TRAM flap involves the use of a vertically oriented flap of rectus abdominus muscle and skin which is removed from the abdomen and tunneled under the remaining abdominal wall and rotated into the mastectomy defect. The overall complication rate has been reported to be 16–18%. Obesity increases the complication rate. Patients who had previous abdominal surgery are not ideal candidates for TRAM flaps. Smoking predisposes a patient to flap necrosis and is a contraindication to surgeons in many centers. Flap procedures involve new surgical scars and the problem of trying to match donor skin-color characteristics. The procedure involves a substantial loss of blood, significant postoperative pain and longer confinement with respect to other reconstructive techniques and a longer length of time for the surgical procedure. There is a greater difficulty in making an early diagnosis of possible local recurrence in comparison with other techniques of breast reconstruction. Complications with the use of TRAM flaps include flap necrosis, liponecrosis, abdominal skin necrosis, abdominal herniation, seroma and infection. Hernia or abdominal laxity occurred in 4% of TRAM flap procedures.

The Ger-Oddsen procedure for breast reconstruction can utilize the tissue expansion devices as disclosed in U.S. Pat. Nos. 5,618,310 and 5,507,775 which are incorporated herein by reference.

One of the geometric shapes of the suture plates for male pattern baldness (FIG. 8) is a convex curve 30. This geometric shape is for male baldness patterns that are round or slightly oblong. The convex shape brings up more skin with hair follicles into the center of male pattern baldness area than to the ends of the defect. Another geometric shape for male pattern baldness shape defines a fairly straight edge for moving tissue into a receding hair line. This geometric shape can be utilized for pre-stretching skin prior to the removal of a nevus, hypertropic scar, keloid or any surgical area that requires tension free skin and subcutaneous tissue prior to removal of a defect.

Figure 1C:
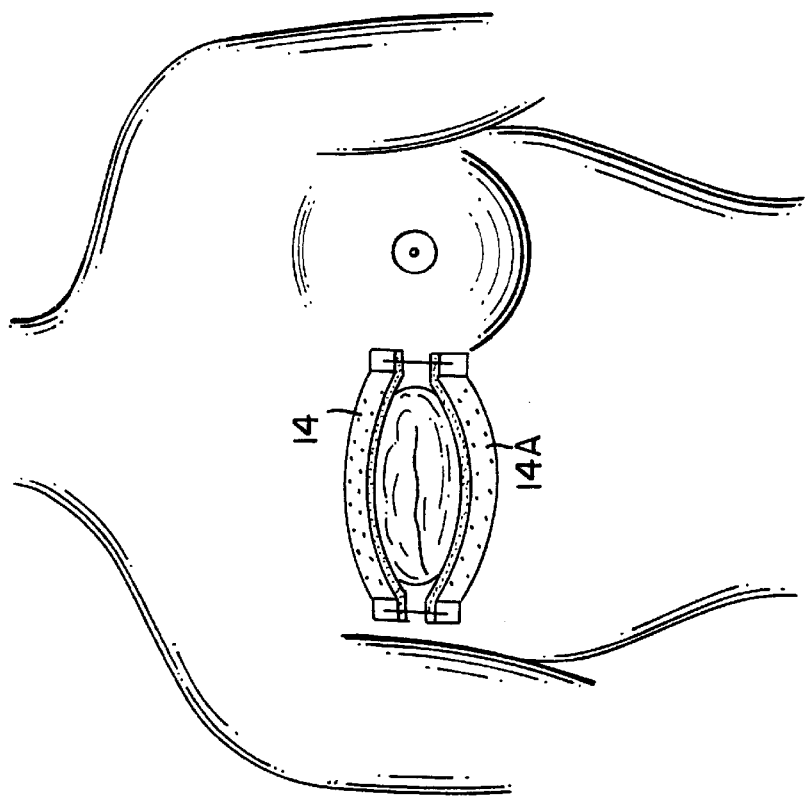
FIG. 1*c* is similar to FIG. 1*b* showing the area about the mastectomy incision a few days after application of said tissue expander device.
Figure 6A:
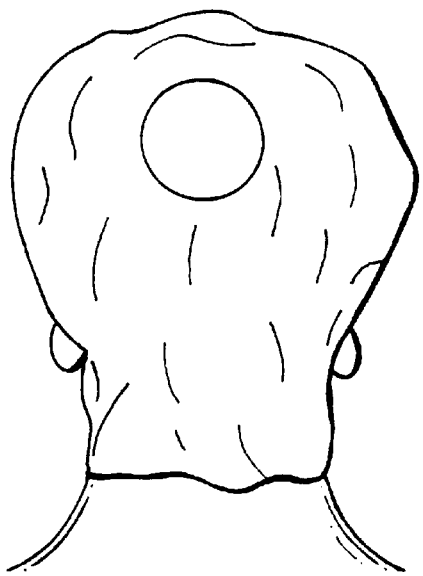
FIG. 6*a* is a rear elevation view of a male patient's head showing male pattern baldness.
Figure 6B:
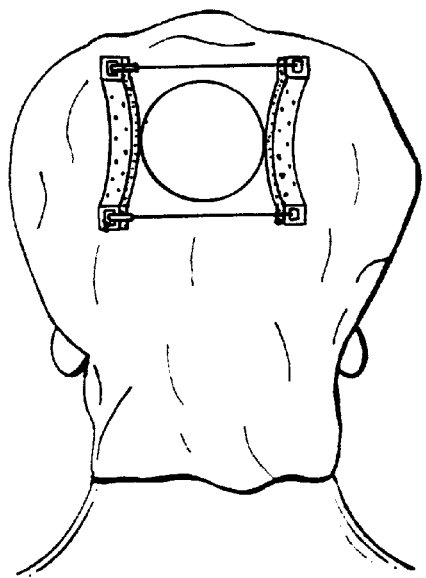
FIG. 6*b* is similar to FIG. 6*a* showing the external tissue expansion device sutured to the scalp adjacent the bald area.
Figure 6C:
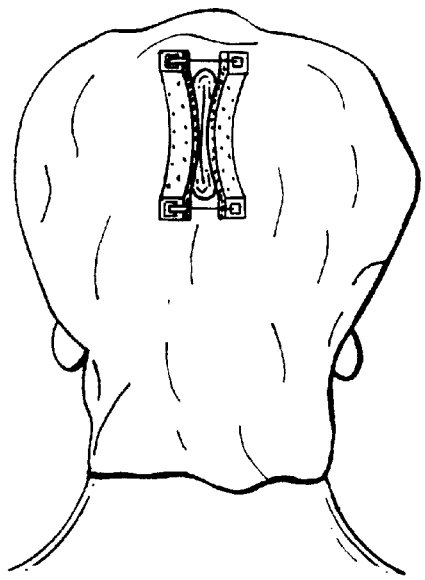
FIG. 6*c* is similar to FIG. 6*b* showing expanded tissue adjacent the bald area a few days after application of said tissue expansion device.
Figure 6D:
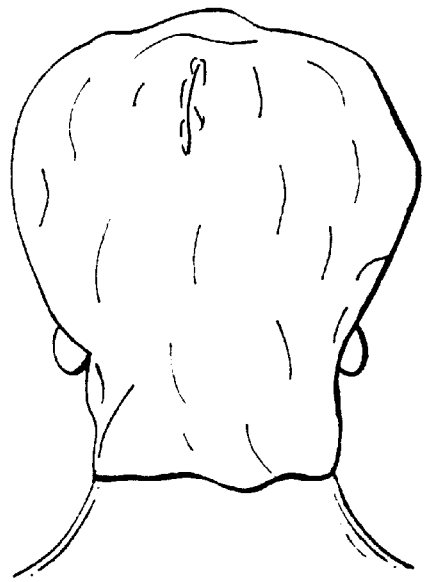
FIG. 6*d* is similar to FIG. 6*c* showing the scalp after the device is removed and after the tissue with no hair follicles has been excised.

When utilizing the new external tissue expansion device the suture plates 14 for breast reconstruction FIGS. 1b, 1c are of a curved geometric shape to approximately conform to the circumference of the definitive implantable prosthesis, contralateral breast or breast shape desired by the patient. Breast reconstruction after mastectomy is achieved as follows. Prior to closure of the mastectomy defect, a silastic plate can be placed subcutaneously in region B of FIG. 1b to prevent the development of adhesions during the external tissue expansion process. The mastectomy incision is sutured closed and the surgeon positions the two suture plates, one above the prospective location of the implantable prosthesis or breast mound and the other below the prospective location of the implantable prosthesis or breast mound. The surgeon manually bends the suture plates to conform to the topography of the area and fastens the suture plates to the skin by sutures through suture holes 18 or by hooks 20. These hooks are about one inch long. The surgeon then inserts the hooks 30 from one suture plate into the holes of the housing of the other suture plate. The suture plates as pulled by the springs apply the spring of a continuous, sustained low grade force of constant magnitude which pulls the suture plates together, and over a time period the suture plates approach each other. As the suture plates approach each other, additional skin and subcutaneous tissue is stretched and expanded from region A (FIG. 1b) and accumulates in region B and the healing of the mastectomy incision occurs in the tension free skin in region B. Over a time period of a few days there is enough additional tension free skin and subcutaneous tissue accumulated in region B to cover the implantable prosthesis or for small breasted women, the breast mound can be shaped into a breast using existing techniques to add additional adipose tissue (if required) by recruiting adipose tissue through liposuction, treating this adipose tissue and reinjecting this treated adipose tissue into the breast mound to shape the breast mound into a breast. This procedure is similar for breast augmentation.

When utilizing a tissue expansion device of U.S. Pat. Nos. 5,618,310 and/or 5,507,775, immediately after closure of the mastectomy incision, one tissue hook of the device is inserted as deep as possible at the inferior mammary fold and the other tissue hook as far superiorly as possible. Four devices are used per breast. Each device applies a continuous, sustained low grade force of constant magnitude to stretch and expand nearby skin and subcutaneous tissue. The devices are secured to the patient and left in place for 2 to 3 days at which time the devices are reapplied to gather additional tissue for another 2 to 3 days. In approximately 4 to 6 days a breast mound of tension free skin and subcutaneous tissue is accumulated between the tissue hooks of the devices for coverage of a breast prosthesis or for small breasted women, the breast mound can be shaped into a breast using existing techniques to add additional adipose tissue (if required) by recruiting adipose tissue through liposuction, treating this adipose tissue and reinjecting this treated adipose tissue into the breast mound to shape the breast mound into a breast.

With the Ger-Oddsen procedure for breast reconstruction there is no incisional surgery for implantation of an internal tissue expander and the complications of internal tissue expansion are eliminated. Tissue expansion can be started immediately and the incisional wound from the mastectomy heals in a tension free environment.

The forces of the internal tissue expander are outward tending to open the sutured mastectomy incision therefore requiring more a time for the sutured incision to heal. The forces of the external tissue expander are inward which allows the sutured mastectomy incision to heal in a tension free environment and tissue expansion can begin immediately. With the Ger-Oddsen procedure the time to obtain tension free skin to cover a prosthesis is reduced from months to days. The abundant amount of skin obtained from the external tissue expansion device permits the implantation of a larger definitive prosthesis (over 300 cc). In many instances for patients with thin tight skin or after radical mastectomy the Ger-Oddsen procedure eliminates the need for a surgical flap procedure. The Ger-Oddsen procedure for small breasted women permits breast reconstruction without the use of any prosthesis, whereby a surgeon expands a breast mound of the patient's own body tissue at a specific location consisting of tension free skin and subcutaneous tissue and shapes this breast mound into a breast using existing technologies for recruitment and transfer of adipose tissue. The Ger-Oddsen procedure eliminates the complications of surgical procedures used to create a breast mound such as the TRAM procedure. The Ger-Oddsen procedure is a minor out-patient surgical procedure with minimal pain, quick recovery and no unsightly surgical scars.

Male Pattern Baldness

As referred to above, the new procedure of this invention can be readily used to reduce or eliminate male pattern baldness.

Inherent in each individual hair follicle is the pathogenesis for common baldness. Hair restoration procedures began with the discovery that hair follicles maintained their integrity and will continue to grow hair at the same rate, texture and color when they are transplanted from one region of the scalp (donor site) to a bald region of the scalp (recipient site). Hair cannot be restored, it can only be rearranged and this places a significant restriction on the hair restoration surgeon since in patients prone to male pattern baldness there is a limited amount of donor site hair.

A common surgical procedure to repair male pattern baldness consists of relocating groups of hair strand called plugs (graft size 3 mm of about 12 hairs), mini grafts (graft size 1.5 mm of about 6 hairs.) or micro-grafts (single to two hairs) to the male pattern baldness site. These transplanted hairs require a donor site, and a scar will appear in the depleted donor area from which each graft that is removed. The number of plugs, micro-grafts or mini grafts required to fill in the loss of hair depends upon the extent of the baldness. The total coverage of 500 to 600 plugs only amounts to an area of 3.5 inches. Single hair transplanting can involve mega sessions of 1,000 hairs with each hair being transplanted individually and the more hairs transplanted the greater the expense of the procedure. The transplantation process usually requires multiple sessions over an 8 to 12 month period, and the hair transplants do not begin to grow hair until 12 weeks after transplantation. There is significant time lost from normal activities and some pain associated with these procedures. In some instances there is scarring and discoloration in the transplanted area that remains long after the transplanted area has fully healed. Of great concern to the hair restoration surgeon is the loss of irreplaceable donor site hair. Hair harvesting techniques at the donor site results in a (5 to 10% loss), and survival of the transplanted hair at the recipient site results in a (5 to 10% loss).

With a limited supply of donor site hair, scalp reduction procedures were developed to decrease the amount of the baldness area prior to hair transplantation. The classic scalp reduction consists of sequential procedures over a time period of many months in which a portion of the scalp are sequentially removed, the remaining portion is stretched and then sutured closed. Skin that has been acutely stretched is under tension and when it is sutured closed tends to stretch back to its original position. Therefore, despite removal of all midscalp bald areas often a significant bald area remained to due the phenomenon of stretchback which limited the use of this procedure.

Recently internal tissue expanders have been used in scalp reduction procedures. The utilization of an internal tissue expander is a multi-stage procedure where first it is surgically placed under the scalp. There is a time period for the scalp incision to heal, then the expander is inflated over a time period, the expander is surgical removed, the expanded bald area of the scalp is excised and the elevated donor site hair is sutured to the scalp. Patient acceptance of this procedure is limited due to the length of time to expand skin (3 to 4 months) and the visual deformity of the expanded implant on the patients' scalp during the expansion process.

Figure 9:
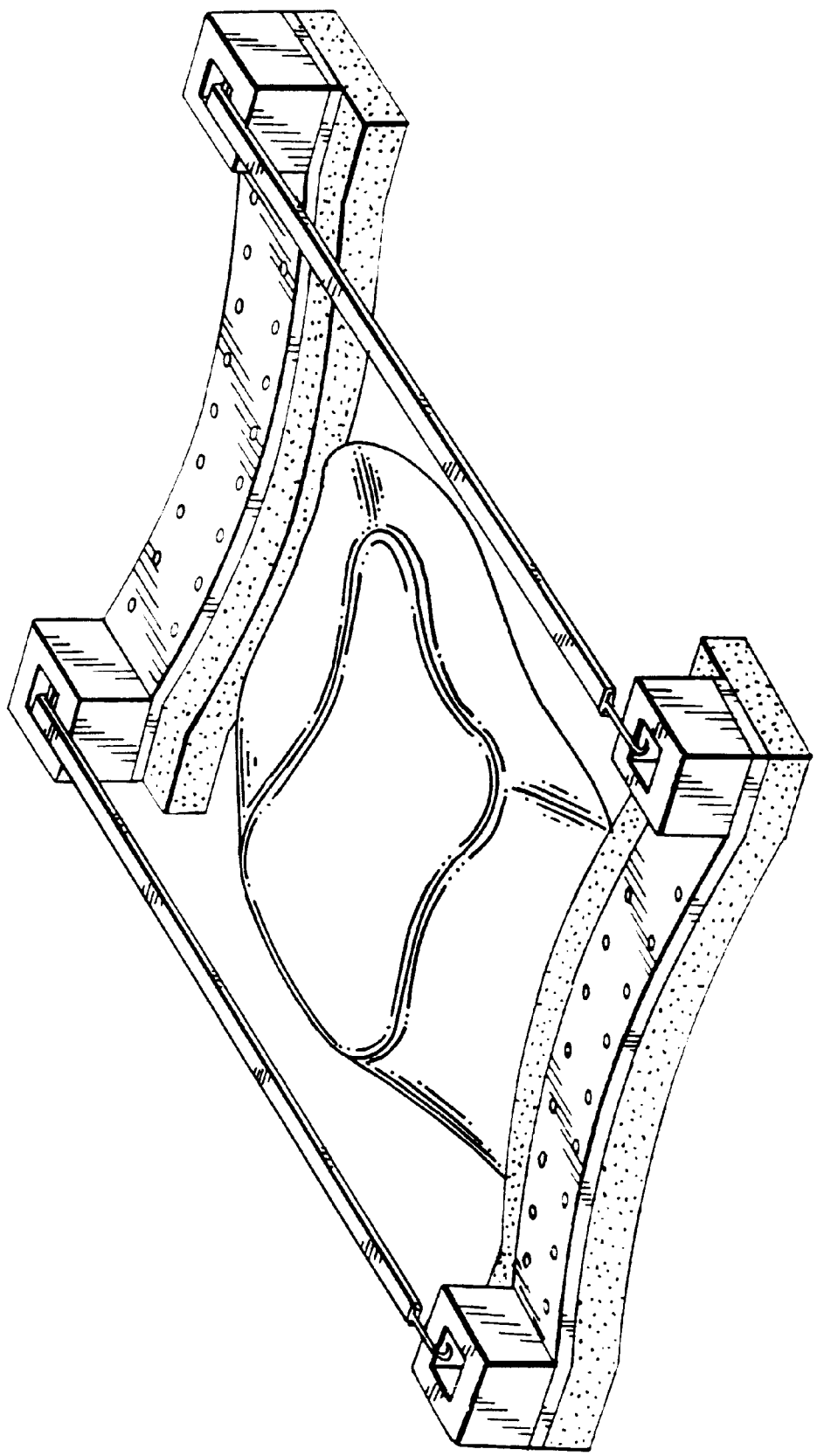
FIG. 9 is similar to FIG. 8 showing the assembled set of tissue expansion plates after an initial time period of application.
Figure 13:
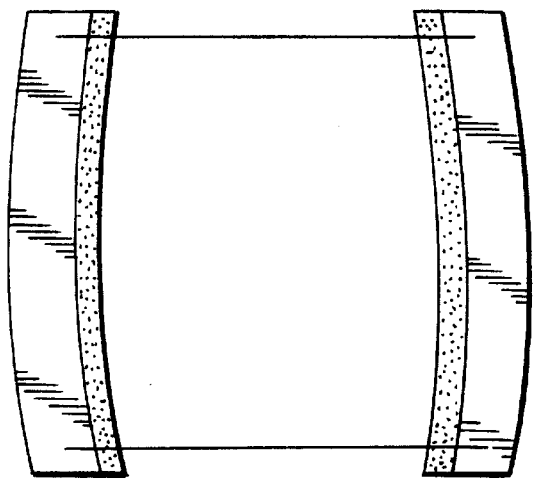
FIGS. 11, 12 and 13 show respectively and schematically the preferred forms of sets of expansion plates for a) male pattern baldness, b) removal of nevi, and c) breast reconstruction.
Figure 11:
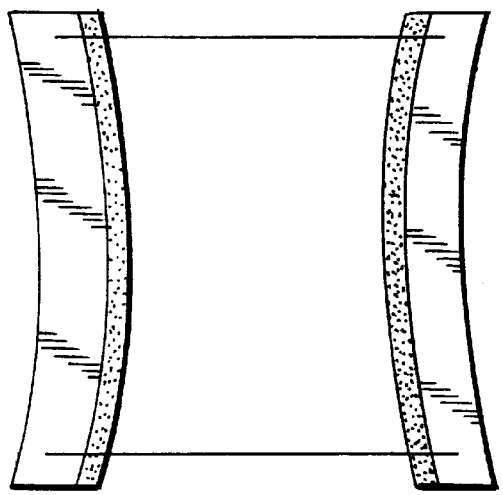
Figure 12:
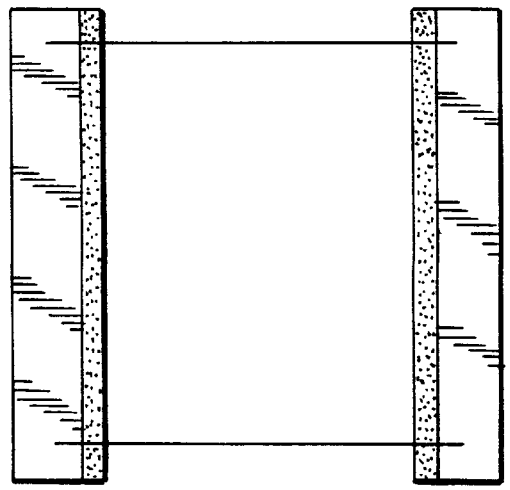

The Ger-Oddsen procedure for male pattern baldness utilizes the general concept from the external tissue expansion devices of U.S. Pat. Nos. 5,618,310 and 5,507,775, but altered as now described below and illustrated in FIGS. 6a–6d and 7–11. One geometric shape of the suture plates for male pattern baldness is a convex curve as seen in the above-referenced Figures for male baldness patterns that are round or slightly oblong. The convex shape brings up more skin with hair follicles into the center of male pattern baldness area than to the ends of the defect. Another geometric shape seen in FIG. 12 defines fairly straight facing edges for moving tissue into a receding hair line male pattern baldness pattern. These shapes are different from the suture plates for breast reconstruction due to the fact that tissue with no hair follicles is going to excised after the external tissue expansion process, whereas the concave shape, see FIGS. 1b, 1c and 13 for breast reconstruction leaves an area for skin and subcutaneous tissue to accumulate. The Ger Oddsen procedure for male pattern baldness consists of the surgeon positioning the suture plates of the external tissue expansion device next to and on each side of the male pattern baldness defect and manually bending the suture plates to conform to the topography of the scalp. The surgeon fastens the suture plates into adipose tissue of donor site hair region A (FIG. 8) of the scalp and inserts the hooks 40 from the spring of one suture plate 42 into the holes 44 of the housing 46 of the other suture plate 48. The springs cause suture plates to apply a continuous, sustained low grade force of constant magnitude which slowly recruits tension free donor site hair towards the balding area over a time period as the suture plates approach each other. As the suture plates approach each other the skin with hair follicles in region A (FIG. 9) is slowly stretched and moved to region B. After a time period of a few days the surgeon removes the external tissue expansion device, excises the tissue with no hair follicles that has accumulated in region B (FIG. 10) and sutures the elevated tension free donor site hair in place.

The expansion devices may be sutured to the patient's scalp or the downward extending hooks may be inserted into donor site 15 and into adipose tissue. The devices apply a continuous, sustained low grade force of constant magnitude and slowly recruits tension free donor site hair towards the balding area. The devices are secured to the patient and left in place for 2 to 3 days at which time the devices are reapplied to elevate donor site hair and gather additional tissue for another 2 to 3 days. In approximately 4 to 6 days a mound of tension free skin and subcutaneous tissue of bald skin and donor site hair is accumulated between the tissue hooks of the devices. The surgeon excises the mound of bald area required by the hair restoration procedure and sutures the elevated tension free tissue containing donor hair in place.

The Ger-Oddsen procedure for male pattern baldness, eliminates the stretchback typical of scalp reduction procedures, since the elevated donor site hair is tension free due to the low grade sustained continuous force of constant magnitude applied by the devices to the scalp for a few days. This allows the fibroelastic bundles of the transposed donor site to reattach themselves at their new elevated location in a tension free environment and no stretchback will occur. The Ger-Oddsen procedure for male pattern baldness eliminates the limitations of internal tissue expanders, by applying an external continuous force of generally constant magnitude slowly over a time period to regions of bald areas and donor site hair. It creates a tension free zone for a scalp reduction procedure in a few days versus the many months of visual deformity of the expanded implant on the patients' scalp required for internal expanders.

Removal of Nevi, hypertrophic scars and keloids

Congenital nevi (birthmarks) are common in the population. These nevi are surgically removed for cosmetic appearance when they are located in facial areas or any exposed surfaces that can be seen by the public. Large nevi are difficult to remove because of the size of the nevus or when located in areas of limited skin elasticity (elbow, arm, knee, leg, etc.) particularly in younger people. Removal of a nevus on the facial area is restricted due to distortions of facial features that can occur after the nevus is removed. The present method for removal of a large nevus requires two or three surgical procedures. In the first surgical procedure a partial portion of the nevus is excised and the wound is closed by suture. After time period for the wound to heal 2 to 4 months, a second surgical procedure is performed to remove another portion of the nevus. This process continues until the nevus is removed.

The Ger-Oddsen procedure for removal of a nevus, hypertrophic scars or keloids can utilize the external tissue expansion devices of U.S. Pat. Nos. 5,618,310 and 5,507,775. The Ger-Oddsen procedure for removal of a nevus utilizing the new external tissue expansion device is as follows. A few days prior to surgery for removal of the nevus the surgeon positions the suture plates of the external tissue expansion device on either side of the nevus, hypertrophic scar or keloid and manually bending the suture plates to conform to the topography of the area. The surgeon fastens the suture plates to the skin and inserts the hooks from the springs of one suture plate into the holes of the housing of the other suture plate. The suture plates apply a continuous, sustained low grade force of constant magnitude to the edges of the nevus, hypertrophic scar or keloid, and over a time period the suture plates approach each other. As the suture plates approach each other an abundant amount of tension free skin and subcutaneous tissue is obtained from the external tissue expansion device between the suture plates. The surgeon removes the suture plates at the time of surgery and is able to excise the entire nevus, hypertrophic scar or keloid and close the wound with the additional tension free skin and subcutaneous tissue..

When utilizing the expansion devices of U.S. Pat. Nos. 5,618,310 and 5,507,775, one tissue hook of the device is inserted into one edge of the nevus, hypertrophic scar or keloid and into adipose tissue and the other tissue hook inserted edge of the nevus, hypertrophic scar or keloid and into adipose tissue on the opposite side of the nevus, hypertrophic scar or keloid. The devices applies a continuous, sustained low grade force of constant magnitude to the edges of the nevus, hypertrophic scar or keloid. The devices are secured to the patient and left in place for 2 to 3 days at which time the devices are reapplied to gather additional tissue for another 2 to 3 days. In approximately 4 to 6 days a mound of tension-free skin and subcutaneous tissue is accumulated between the tissue hooks of the devices. The surgeon excises the nevus, hypertrophic scar or keloid and closes the incision with the additional tension-free skin and subcutaneous tissue that has accumulated between the tissue hooks.

The Ger-Oddsen procedure removes a nevus, hypertrophic scars or keloids with no distortion of surrounding features by utilizing the additional tension-free skin and subcutaneous tissue obtained from the external tissue expansion process. The time required to remove a large nevus, hypertrophic scar or keloid is reduced from several months to days and the multiple surgical procedures previously required is reduced to one. Typical time periods for application of the tissue expansion plates are about 4–7 days for breast reconstruction, about 4–12 days for male pattern baldness, and about 4 days for nevi removal. These time periods include re-setting the expansion plates about every two days to expand more skin and underlying subcutaneous tissue. The closed wound heals in a tension-free environment which is particularly important for hypertrophic scars or keloids since it has been found that one of the factors for initiation of a keloid or hypertropic scar is tension.

The embodiments of the invention described herein are merely examples of the invention. Many variations and equivalents are possible within the spirit and scope of the claims appended hereto.

What is claimed is:

1. An external expansion device applicable to an area of a patient's skin and underlying subcutaneous tissue to expand said area to obtain additional tension free skin and subcutaneous tissue, comprising
   a. a set of first and second tissue expansion plates, each of said expansion plates having a skin-engaging surface and being deformable from an initial configuration to a second configuration different from said initial configuration,
   b. securing means on each of said plates for securing said plates to a patient's skin and underlying subcutaneous tissue, each of said plates having said initial configuration after, said skin-engaging surface is conformed to said skin and secured thereto;
   c. at least one force application means,
   d. said plates being positionable and spaced apart on and secured to an area of patient's skin and underlying subcutaneous tissue with said force application means on said first plate extended and connected to said second plate, said force application means exerting a force urging said first and second plates and skin and underlying subcutaneous tissue to which each plate is secured to move toward each other.

2. A device according to claim 1 wherein said force application means exerts a continuous constant magnitude force regardless of the distance between said plates.

3. A device according to claim 1 wherein said securing means comprises at least one hook with a sharp point extending downward from the bottom of said expansion plate.

4. A device according to claim 3 wherein said securing means comprises a plurality of said hooks spaced apart lengthwise on said expansion plate.

5. A device according to claim 3 wherein said expansion plate and said hooks comprise stainless steel, said hooks being rigidly fixed to said plate.

6. A device according to claim 1 wherein said force application means is a Negator® brand spring.

7. An external tissue expansion device applicable to an area of a patient's skin and underlying subcutaneous tissue to expand said area to obtain additional tension free skin and subcutaneous tissue comprising
   a. a set of first and second tissue expansion plates,
   b. securing means on each of said tissue expansion plates for securing said plate to a patient's skin and underlying subcutaneous tissue, wherein each of said expansion plates defines a plane which permits deformation transverse of said plane and which resists plastic deformation in the direction of said plane,
   c. at least one force application means,
   d. said tissue expansion plates being positionable and spaced apart on and secured to an area of a patient's skin and underlying subcutaneous tissue with said force application means on said first plate extended and connected to said second plate, said force application means exerting a force urging said first and second plates and skin and underlying subcutaneous tissue to which each plate is secured to move toward each other.

8. An external tissue expansion device applicable to an area of a patient's skin and underlying subcutaneous tissue to expand said area to obtain additional tension free skin and subcutaneous tissue, comprising
   a. a set of first and second tissue expansion plates,
   b. securing means on each of said plates for securing said plate to a patient's skin and underlying subcutaneous tissue, wherein each of said expansion plates defines a plane which permits plastic deformation transverse of said plane and which resists plastic deformation in the direction of said plane,
   c. at least one force application means,
   d. said plates being positionable and spaced apart on and secured to an area of patient's skin and underlying subcutaneous tissue with said force application means on said first plate extended and connected to said second plate, said force application means exerting a force urging said first and second plates and skin and underlying subcutaneous tissue to which each plate is secured to move toward each other,
   wherein each of said expansion plates is an elongated laminate comprising a thin strip of solid material on top and a strip of cushion material on the bottom.

9. A device according to claim 8 wherein said strip of solid material comprises stainless steel.

10. A device according to claim 8 wherein said cushion material comprises soft compressible foam.

11. A device according to claim 10 wherein said cushion comprises a material selected from the group consisting of compressible thermoplastic rubber, adhesive backed polyester or polyurethane foam.

12. A device according to claim 8 wherein said cushion has width greater than that of the solid strip.

13. An external tissue expansion device applicable to an area of a patient's skin and underlying subcutaneous tissue to expand said area to obtain additional tension free skin and subcutaneous tissue, comprising
   a. a set of first and second tissue expansion plates
   b. securing means on each of said plates for securing said plate to a patient's skin and underlying subcutaneous tissue,
   c. at least one force application means,
   d. said plates being positionable and spaced apart on and secured to an area of a patient's skin and underlying subcutaneous tissue with said force application means on said first plate extended and connected to said second plate, said force application means exerting a force urging said first and second plates and skin and underlying subcutaneous tissue to which each plate is secured to move toward each other,
   wherein each of said expansion plates defines a generally elongated rectangle with one front edge defined by length and thickness, said front edges of said plates having a convex curvature, and each of said expansion plates when positioned generally parallel and spaced apart from the other has its front edge facing the front edge of the other plate.

14. An external tissue expansion device applicable to an area of a patient's skin and underlying subcutaneous tissue to expand said area to obtain additional tension free skin and subcutaneous tissue, comprising
   a. a set of first and second tissue expansion plates,
   b. securing means on each of said plates for securing said plate to a patient's skin and underlying subcutaneous tissue,
   c. at least one force application means,
   d. said plates being positionable and spaced apart on and secured to an area of a patient's skin and underlying subcutaneous tissue with said force application means on said first plate extended and connected to said second plate, said force application means exerting a force urging said first and second plates and skin and underlying subcutaneous tissue to which each plate is secured to move toward each other, wherein each of said expansion plates defines a generally elongated rectangle with one front edge defined by length and thickness, said front edges of said plates having a concave curvature, and each of said expansion plates when positioned generally parallel and spaced apart from the other has its front edge facing the front edge of the other plate.

15. An external tissue expansion device applicable to an area of a patient's skin and underlying subcutaneous tissue to expand said area to obtain additional tension free skin and subcutaneous tissue, comprising a. a set of first and second tissue expansion plates b. securing means on each of said plates for securing said plate to a patient's skin and underlying subcutaneous tissue, c. at least one force application means, d. said plates being positionable and spaced apart on and secured to an area of a patient's skin and underlying subcutaneous tissue with said force application means on said first plate extended and connected to said second plate, said force application means exerting a force urging said first and second plates and skin and underlying subcutaneous tissue to which each plate is secured to move toward each other, wherein said securing means comprises a plurality of apertures extending through the thickness of each said expansion plates adapted for receiving suture material therethrough.

16. A method for obtaining additional skin and underlying subcutaneous tissue and locating this additional tissue at and adjacent to a patient's mastectomy incision prior to implantation of a breast prosthesis for breast augmentation or for breast reconstruction after mastectomy, comprising:

a. engaging two regions of skin and subcutaneous tissue generally adjacent and spaced from and on opposite sides of said mastectomy incision, and b. urging said engaged regions of skin and subcutaneous tissue towards each other where said urging comprises applying a generally continuous external force of generally constant magnitude for a time period of about 4 to 7 days, thereby accumulating additional skin and subcutaneous tissue at and adjacent to said mastectomy incision to cover a breast prosthesis.

17. A method according to claim 16 comprising the further step of shaping said accumulated skin and subcutaneous tissue into a breast mound.

18. A method for expanding a patient's skin with hair follicles and locating this expanded skin with hair follicles to a bald region of skin for repair of male pattern baldness, comprising the steps:

a. engaging two spaced apart regions of skin with hair follicles which bound a bald region, b. urging said engaged regions of skin with hair follicles toward each other where said urging comprises applying a generally continuous external force of generally constant magnitude, c. applying said force over a time period of about 4–12 days to elevate and accumulate additional skin with hair follicles adjacent said bald region, and d. excision of said bald region and suturing together the edges of skin with hair follicles to cover said bald region.

19. A method for expanding a region of unpigmented skin of a patient and locating this unpigmented skin to a region of skin with pigmentation for removal of a nevus or tattoo, comprising the steps:

a. engaging two spaced apart regions of unpigmented skin which bound a region of skin with pigmentation, b. urging said regions of unpigmented skin toward each other where said urging comprises applying a generally continuous external fore of generally constant magnitude, c. applying said force over a time period of about 4 days to elevate and accumulate additional unpigmented skin adjacent said region of pigmented, skin, and d. excision of said pigmented skin and suturing together the edges of unpigmented skin.

20. A method of breast reconstruction utilizing a patient's own body tissue and without using a prosthesis, by obtaining additional skin and underlying subcutaneous tissue and locating this additional tissue at and adjacent to a patient's mastectomy incision, comprising the steps:

a. engaging two regions of skin and subcutaneous tissue generally adjacent and spaced from and on opposite sides of said mastectomy incision, b. urging said engaged regions of skin and subcutaneous tissue towards each other where said urging comprises applying a generally continuous external force of generally constant magnitude for a time period of about 4 to 7 days, thereby accumulating additional skin and subcutaneous tissue at and adjacent to said mastectomy incision, and c. applying said generally continuous external force of generally constant magnitude slowly over a time period to provide a tension free region for healing a mastectomy incisional wound, and d. shaping of said breast mound into a breast.

* * * * *